United States Patent [19]

Ryder et al.

[11] Patent Number: 4,735,203

[45] Date of Patent: Apr. 5, 1988

[54] RETRACTABLE LANCET

[75] Inventors: Francis E. Ryder; Stephen P. Lisak; Harold L. Purdy, all of Arab, Ala.

[73] Assignee: Ryder International Corporation, Arab, Ala.

[21] Appl. No.: 941,164

[22] Filed: Dec. 12, 1986

[51] Int. Cl.⁴ .......................................... A61B 17/32
[52] U.S. Cl. ................................. 128/314; 128/329 R
[58] Field of Search .................. 128/314, 315, 329 R, 128/330; 604/156, 157, 134–137; 30/366, 367, 155

[56] References Cited

U.S. PATENT DOCUMENTS

| | | |
|---|---|---|
| 4,450 | 4/1846 | Gemrig . |
| 55,620 | 6/1866 | Capewell . |
| 677,756 | 7/1901 | Caldwell . |
| 1,135,465 | 4/1915 | Pollock . |
| 2,694,398 | 11/1954 | LaDrigue . |
| 2,864,370 | 9/1955 | Alvos . |
| 3,358,689 | 12/1967 | Higgins . |
| 3,741,197 | 6/1973 | Sanz et al. ............................ 128/2 F |
| 3,903,887 | 9/1975 | Antoshkiw .......................... 128/221 |
| 4,078,552 | 3/1978 | Chen et al. ........................... 128/2 G |
| 4,139,011 | 2/1979 | Benoit et al. ......................... 128/329 |
| 4,203,446 | 5/1980 | Hofert et al. ........................ 128/329 |
| 4,358,539 | 11/1982 | Bittings ................................ 435/301 |
| 4,375,815 | 3/1983 | Burns ................................... 128/314 |
| 4,379,456 | 4/1983 | Cornell et al. ...................... 128/314 |
| 4,388,925 | 6/1983 | Burns ................................... 128/314 |
| 4,445,510 | 5/1984 | Rigby ................................... 128/329 |
| 4,449,529 | 5/1984 | Burns et al. ......................... 128/314 |
| 4,452,243 | 6/1984 | Leopoldi et al. .................... 128/314 |
| 4,469,110 | 9/1984 | Slama ................................... 128/314 |
| 4,628,929 | 12/1986 | Intengan et al. .................... 128/314 |

Primary Examiner—Dalton L. Truluck
Assistant Examiner—F. Wilkens
Attorney, Agent, or Firm—Trexler, Bushnell, Giangiorgi & Blackstone, Ltd.

[57] ABSTRACT

A retractable, non-reusable bleeding time lancet apparatus comprises a housing having an end opening, a blade, and a carrier for fixedly mounting the blade and mounted in the housing for sliding motion toward and away from the end opening. A resilient biasing member is mounted in the housing in a prestressed condition and is operatively coupled for selectively urging the carrier for achieving sliding motion toward and away from the housing end opening. A non-resettable release member normally retains the biasing member in its prestressed condition and is selectively activatable for releasing the resilient biasing member to urge the carrier in a sliding motion for projecting at least a cutting edge of the blade through the end opening. Cooperating surfaces on the housing and carrier define respective limits of sliding motion of the carrier corresponding to extended and retracted positions of the blade cutting edge relative to the housing end opening. The resilient biasing member is operatively engaged with the carrier for achieving a compound sliding movement of the carrier comprising an initial portion including extension of the carrier for projecting the blade cutting edge outwardly of the housing end opening, immediately followed by a second portion including retraction of the carrier for retraction of the blade cutting edge back into the housing.

20 Claims, 5 Drawing Sheets

RETRACTABLE LANCET

BACKGROUND OF THE INVENTION

The invention concerns a lancet assembly, and more particularly concerns an automatically retractable non-reusable lancet assembly.

Sharp pointed or blade-like lancets, as they are generally known in the art, are employed to make a quick puncture or penetration of the skin of a patient to cause a small flow of blood. Various tests require a relatively small amount of blood, for example a drop smeared upon a slide or the like for microscopic viewing, such that the amount of blood flowing from a finger prick of this type is normally sufficient. Also, various bleeding time tests are often employed in which the time running from the puncture of the skin until the cessation of blood flow is measured. Such bleeding time provides a measure from which, by reference to tables or the like, the clotting factors and/or other such relevant information concerning a patient's blood chemistry can be estimated. One such bleeding time test, referred to in the art as the Ivy technique, determines the rate of blood loss or bleeding time. One of the prior art blade-like puncturing devices developed for use in this test is shown in U.S. Pat. No. 4,078,552 to Chen et al.

Because the nerve endings in the finger tip area are quite sensitive, even such minimal skin punctures may be quite irritating and/or painful. In order to minimize the discomfort associated with such tests, it is desirable to make the puncture or penetration of the skin by the lancet as rapid and short-lived as possible. Moreover, in order to achieve some degree of standardization and repeatability as to the above-described bleeding time type of test, it is desirable that the lancet be designed so that the speed, effective time of penetration, and depth of penetration are standardized and repeatable from one lancet device to the next.

Various spring loaded lancets are known, some of which provide spring-loaded firing for standardization of the forces, velocities, and depth of penetration, and some of which provide spring-loaded, retractable features. For example, such spring-loaded and/or retractable lancets are shown in U.S. Pat. to Burns, Nos. 4,375,815 and 4,388,925 as well as in the U.S. Pat. to Burns No. et al, 4,449,529.

The retractable feature of some of these lancets is also desirable, in that it prevents reuse of the lancet, and requires disposal of the same after but one use. This is important for at least two reasons: firstly, for health and sanitary reasons it is inadvisable to reuse the same lancet on a second patient; and secondly, some technicians might reuse the blade of a preloaded or spring-loaded lancet after an initial firing thereof without restressing or preloading the spring, but rather by merely manually making the puncture, thus failing to take advantage of the preloaded, controlled force and velocity of the action thereof. In the second case, some of the prior art devices leave the cutting edge or point extended from the body or housing of the lancet after firing and may or may not permit reloading or recompression of the springs or other members which accomplish firing.

Some other lancets utilize a multiple spring arrangement, such as those shown in some of the Burns or Burns et al patents noted above. However, such assemblies are relatively complex and require a number of interfitting parts which are relatively difficult to manufacture and accurately assemble. Moreover, the use of two springs, one for firing of the lancet point or blade and a second for retracting the same after firing, presents a number of problems in accurately reproducing the tensile strengths and behavior, both in compression and upon release, of two oppositely acting springs. These factors can be difficult to uniformly reproduce in practice, at least in a relatively inexpensive, disposable product. This difficulty is due not only to the problems in selecting and properly mounting and pretensioning the springs themselves, but also in the difficulty of maintaining uniformity of housing or other casing parts within which the springs are mounted, maintaining accurate dimensions, controlling frictional forces, and the like.

In order to overcome the foregoing problems and address the foregoing considerations, we have devised a novel retractable, non-reusable bleeding time lancet apparatus. Our apparatus comprises a housing having an end opening, a blade, and a carrier for fixedly mounting the blade and mounted in the housing for sliding motion toward and away from the end opening. A resilient biasing member is mounted in the housing in a prestressed condition and is operatively coupled for selectively urging the carrier for achieving sliding motion toward and away from the housing end opening.

A non-resettable release member normally retains the biasing member in its prestressed condition and is selectively activatable for releasing the resilient biasing member to urge the carrier in a sliding motion for projecting at least a cutting edge of the blade through the end opening. Cooperating surfaces on the housing and carrier define respective limits of sliding motion of the carrier corresponding to extended and retracted positions of the blade cutting edge relative to the housing end opening.

The resilient biasing member is operatively engaged with the carrier for achieving a compound sliding movement of the carrier comprising an initial portion including extension of the carrier for projecting the blade cutting edge outwardly of the housing end opening, immediately followed by a second portion including retraction of the carrier for retraction of the blade cutting edge back into the housing.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like reference numerals identify like elements, and in which:

DETAILED DESCRIPTION OF THE ILLUSTRATED EMBODIMENT

Figure 1:
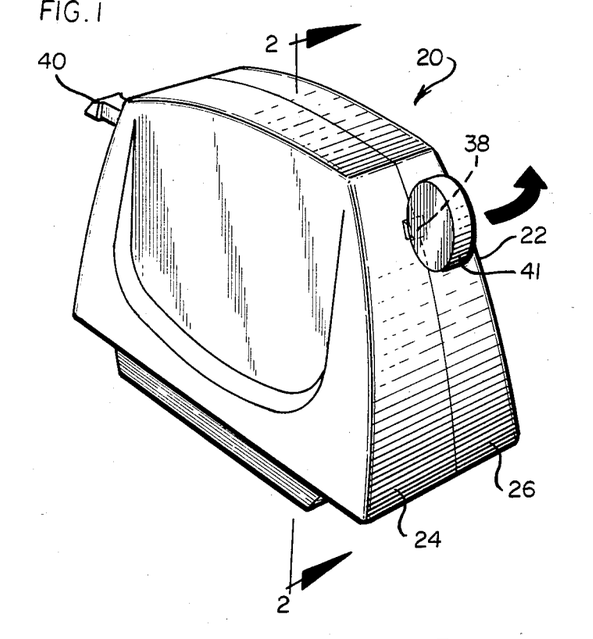
FIG. 1 is a perspective view of a retractable lancet in accordance with the invention.

Referring now to the drawings, and initially to FIG. 1, a retractable, nonreusable bleeding time lancet in accordance with the invention is designated generally by the reference numeral 20. In its fully assembled form as viewed in FIG. 1, the lancet 20 includes a housing 22 which, in the preferred form illustrated, is comprised of two similar and complementary shell portions 24, 26 each of which define substantially one-half of the housing, and more particularly define respective front and rear halves thereof. Aside from housing 22, little else is visible in FIG. 1, which it should be noted is shown greatly enlarged over the actual size of the apparatus. In use, the assembled lancet generally appears substantially as seen in FIG. 1. That is, the puncturing or blade member thereof is only fired or ejected therefrom for a relatively short time, on the order of a fraction of one second, and is immediately retracted, such that it is difficult even to visually observe the brief extension of the blade in practice.

Figure 2:
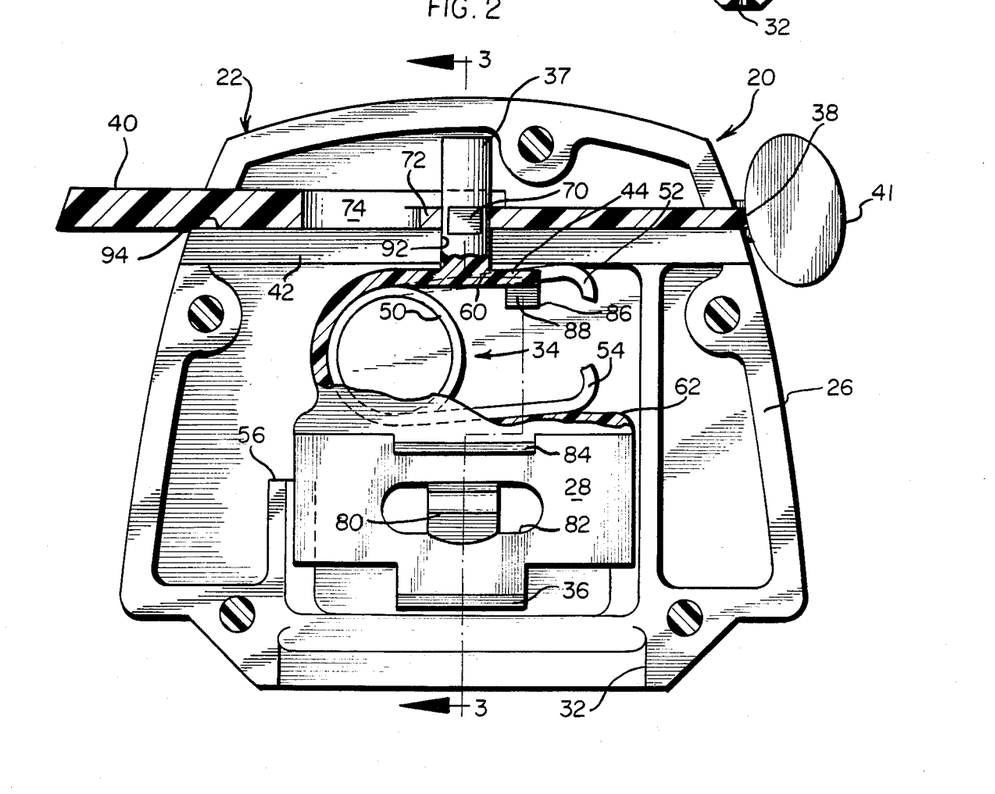
FIG. 2 is an enlarged, developmental view, taken generally along the line 2—2 indicated in FIG. 1, and illustrating details of the internal construction thereof.
Figure 3:
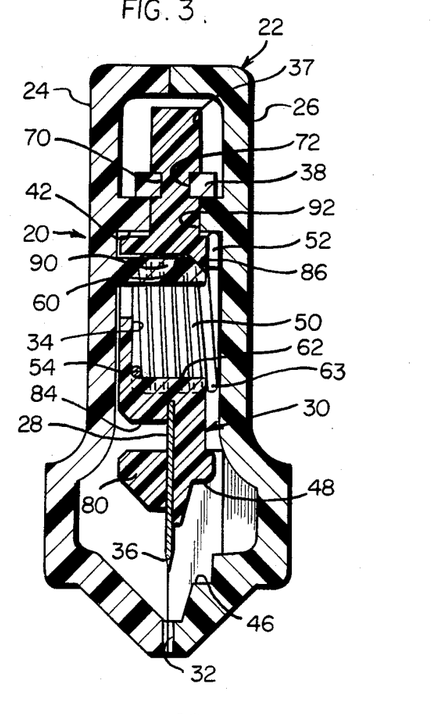
FIG. 3 is a developmental view taken generally along the line 3—3 of FIG. 2.

Referring now also to FIGS. 2 and 3, these further enlarged views of lancet 20 further reveal a blade or blade means 28 and carrier means 30 which fixedly mounts the blade 28. The carrier 30 is mounted in the housing 22 for slidable movement generally toward and away from an end opening 32 of the housing, through which the blade 28 briefly projects when the device is operated, to puncture the skin of a patient. Resilient biasing means which, in the illustrated embodiment, comprises a single coil-type spring 34, is mounted in the housing 22 in a prestressed condition as will be more fully explained hereinbelow. This resilient biasing means or spring 34 is further operatively coupled with the carrier 30 for resiliently selectably urging the same in a sliding motion toward and away from the housing end opening.

A non-resettable release means in the illustrated embodiment comprises a projecting post or trigger member or portion 37 on the carrier 30 and a cooperating clip member 38. These members are operatively coupled for normally retaining the biasing means or spring 34 in its prestressed condition. A frangible tab 41 is molded into one or both housing halves 24, 26 in a position so as to generally overlie the outwardly projecting end of clip 38. Absence of this breakaway tab will indicate that the device has been used and is to be discarded. This acts as a further back-up feature to the nonresettable nature of the device as described herein However, it will be seen that depression of a projecting outer end 40 of the clip member 38 will break tab 41 and release the projecting post or trigger member 37 from its retained condition to permit this prestressed spring 34 to generally uncoil or move toward a relaxed position thereof. When the spring 34 is thus released from its prestressed condition, it urges the carrier 30 initially toward the opening 32 and an extended position thereof wherein the blade 28 or at least an endmost cutting edge 36 thereof extends or projects through the opening 32 for puncturing the skin of the patient.

The housing 22 and carrier 30 further have cooperating means formed thereon in the form of respective abutting or stop surfaces 42, 44 and 46, 48 for defining respective limits of sliding motion of the carrier relative to the housing. These limits of motion correspond to the retracted position of the blade shown in FIGS. 2 and 3 and the extended or projecting position shown in FIG. 4, to which reference is also invited.

Figure 4:
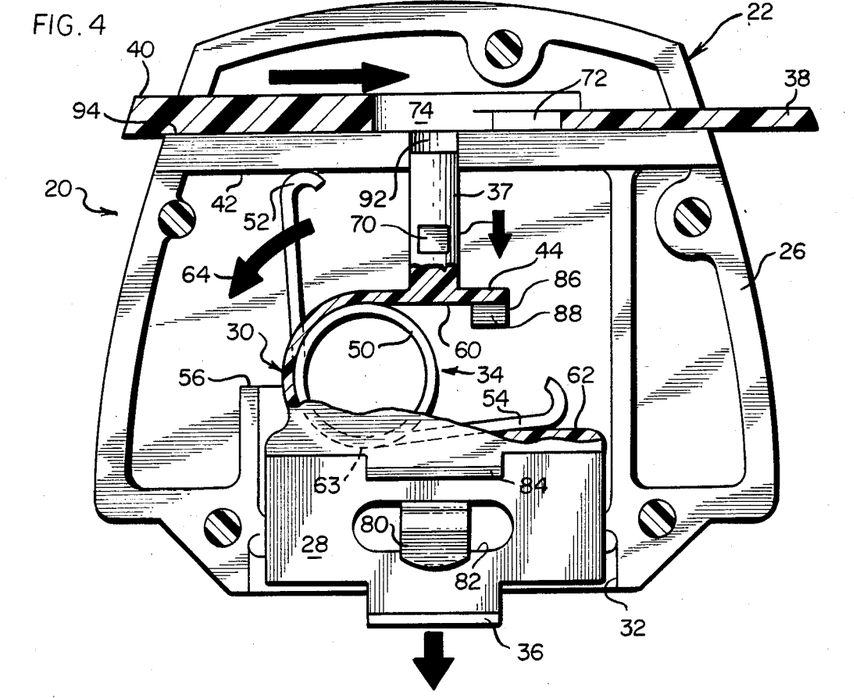
FIG. 4 is a view similar to FIG. 2 and illustrating an initial portion of a compound movement of the lancet device of the invention upon firing thereof.
Figure 5:
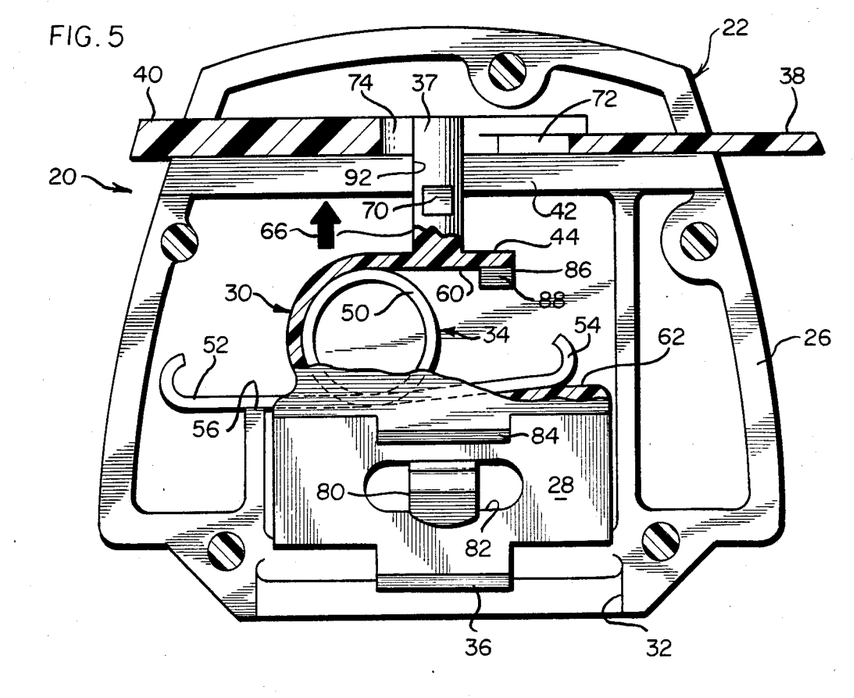
FIG. 5 is a view similar to FIGS. 2 and 4 and illustrating a second portion or retraction portion of the compound movement of the lancet device of the invention upon firing thereof.

In accordance with the invention and referring now also to FIGS. 4 and 5, the sliding motion of the carrier caused by release of the spring 34 is a two-part or compound type of motion This motion comprises an initial portion including extension or urging of the carrier 30 in the direction of opening 32 for extension or projection of the blade 28 or at least the cutting edge 36 thereof exteriorly of the housing, as illustrated in FIG. 4. A second portion of this motion immediately follows the extension shown in FIG. 4, and this second portion comprises retraction of the carrier 30 for corresponding retraction of the blade cutting edge 36 back into the housing. This second portion of the compound motion is illustrated in FIG. 5. It will be noted that the novel coil spring arrangement in accordance with the invention provides this compound, or serial, bi-directional sliding motion as it travels from the prestressed condition illustrated in FIG. 2, to or at least toward a relaxed condition thereof, as illustrated in FIG. 5. That is, while it is not necessary that any tension or stress remain upon the spring when it assumes the position in FIG. 5, some amount of tension or stress may, nonetheless, remain without departing from the invention.

Turning now more particularly to the details of the preferred embodiment illustrated in FIGS. 1 through 7, the coil spring comprises a helical body portion 50 and at least one outwardly projecting free end portion or arm 52. In the illustrated embodiment a second, opposite outwardly projecting free end or arm 54 is also provided. Operatively engaging the spring or biasing means for achieving the above-described motion of the carrier during release of the spring from its tensioned or prestressed condition shown in FIG. 2, are the first abutment surface 42 described previously and a second abutment surface 56. This second abutment surface 56 comprises a projecting rim or rib portion of an interior of the housing 22 which defines a surface which is generally parallel and spaced from, and mutually inwardly facing, with respect to surface 42. The surface 56 is relatively closer to end opening 32 than the first abutment surface 42.

The means for operatively engaging the spring further include a compartment 60 formed within the carrier 30 for receiving or mounting the body portion 50 of the spring. This compartment has a floor or lower surface portion 62 which also abuts the opposite free end or arm 54 of the spring.

Accordingly, as best appreciated upon viewing in sequence, FIGS. 2, 4 and 5, initially, as shown in FIG. 2, the free end or arm 52 of the spring abuts housing surface 42. Upon release of the clip 40, this arm 52 continues to abut and push against fixed wall or surface 42 so as to thereby drive the remainder of spring and the carrier 30 in which the body 54 is mounted generally downwardly or toward the end opening 32. The effective projection or length of arm 52 is selected to result in extension of the cutting portion 36 of the blade 28 outwardly of the opening 32 in the housing when the arm reaches a generally fully extended or substantially vertically oriented position relative to the housing and surface 42, as illustrated in FIG. 4.

In order to permit some compliance or "play" of the spring to assure clearance of the arm 52 relative to surface 42 during firing, a last or outermost coil 63 of the spring extends outwardly of the floor or lower surface portion 62 of the compartment 60. This allows for some manufacturing variations or tolerances in the length of the arm 52 and in the thicknesses and relative locations of the respective stop surfaces 42 and 56. That is, this compliance or play allowed by the projection of the coil 63 outwardly of the housing floor 62 permits this last coil to deform downwardly somewhat as the arm 52 rotates in engagement with surface 42 and prevents the arm from "hanging up" on surface 42.

Thereafter, the arm continues in motion, as indicated by arrows 64, continuing to release the tension or pre-stressing forces upon the spring until arm 52 comes into engagement with the opposite or lower abutment surface or rib 56. Thereupon, the arm 52 tends to move in the direction that will produce a relaxed state for the spring 34. In the condition shown in FIG. 5, the two arms 52 and 54 extend substantially in a straight line or 180 degrees opposite relative to the body 50 and at either end thereof.

It will be noted, however, that in order to achieve this last position (FIG. 5), the body of the spring 50 must again be drawn somewhat upwardly from the position illustrated in FIG. 4. This results in the carrier 30 being drawn upwardly with spring body 50 since the latter is held mounted in compartment 60 within the carrier. This motion is indicated generally by arrow 66 in FIG. 5. This in turn results in retraction of the blade 28, or at least the cutting edge 36 thereof back interiorly of the opening 32 and within the housing.

It should be noted that as the entire mechanism including the spring and carrier and the trigger projection or post 37, as well as blade 28, are entirely within the housing at the end of firing or release of the spring as shown in FIG. 5. No part or parts are accessible to permit resetting of the assembly to the condition shown in FIG. 2. In this regard, it will be seen that the trigger post and clip 38 cooperate by means of a pair of notches or slots 70 formed in the trigger post and a cooperating elongate slot 72 formed in the clip 38 which defines shoulders for engaging the slots 70. When the clip 38 is depressed by means of manual activating tab 40 generally to the right as shown in FIGS. 2, 4 and 5, the gripping slot 72 of clip 38 is pushed out of engagement with grooves or slots 70 and an enlarged through opening portion 74 of the clip is brought into registry with post 37. This permits the post 37 to travel freely through opening 74 in response to the unwinding motion of the spring 34. Moreover, aside from tab 40 all of the foregoing parts are inaccessible from the exterior of the housing to prevent any attempt to reset or reuse the device, or to later force the blade 28 back outwardly of opening 32.

In this latter regard, the spring 52, although in a relaxed or nearly relaxed state, reliably holds the blade in the retracted position shown in FIG. 5.

Preferably, the coil spring 34 is selected and/or formed so as to provide a predetermined controlled amount of force and acceleration to the blade for maintaining a controlled amount of force and time of contact of the blade cutting edge with the skin of the patient. Also, the amount of extension of the blade relative to the housing shown in FIG. 4 is selected to achieve the desired depth of penetration of skin to carry out the bleeding time tests in accordance with the standard so-called Ivy technique.

Figure 6:
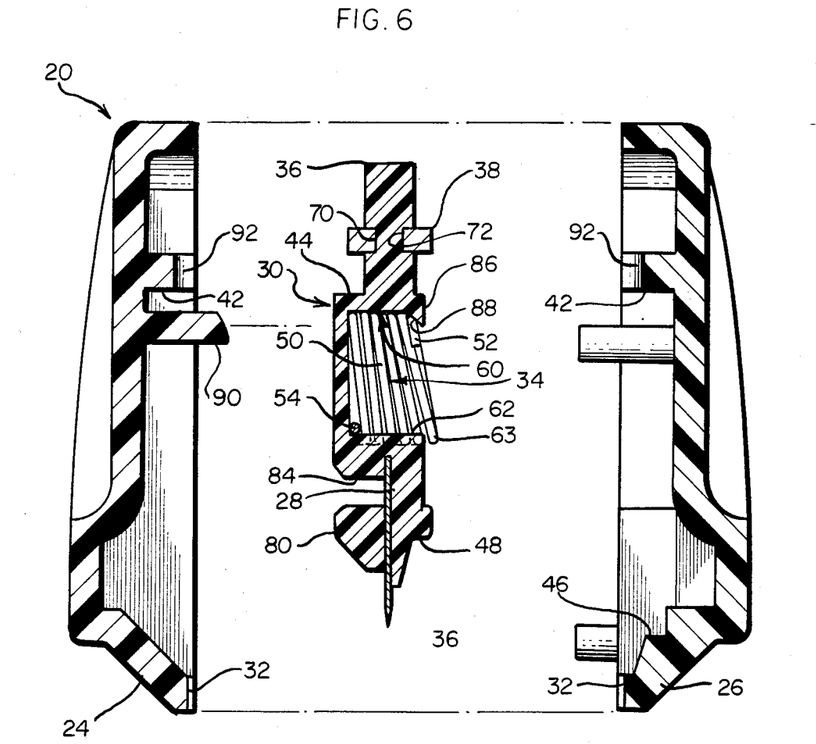
FIG. 6 is an exploded view similar to FIG. 3, and illustrating the assembly of the components of the lancet of the invention.
Figure 7:
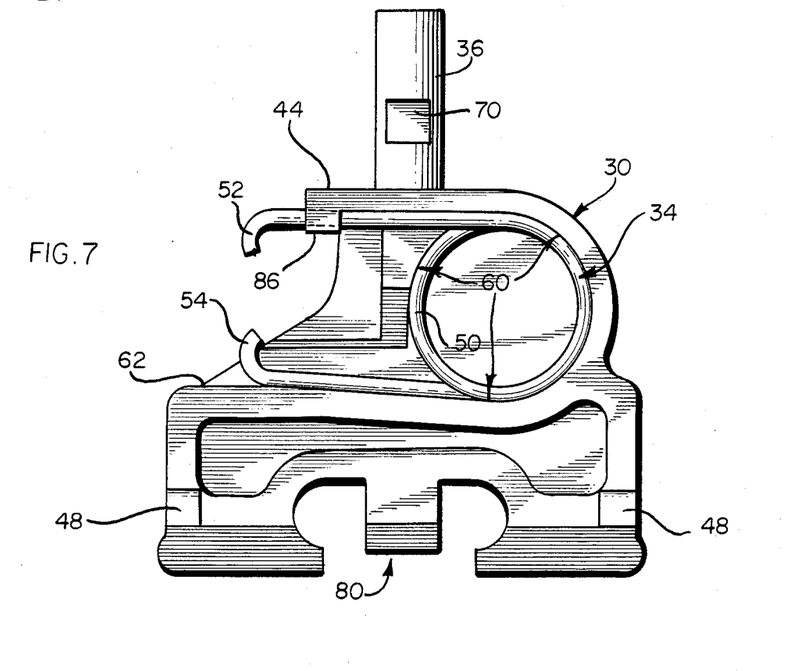
FIG. 7 is a side elevation of a preassembled spring and blade carrier portion of the lancet apparatus of the invention, somewhat enlarged from the previous views.

In accordance with a further feature of the invention, and referring now also to FIGS. 6 and 7, a novel arrangement is provided for simplifying and facilitating assembly of the lancet device of the invention. Initially, the carrier means 30 will be seen to be configured for receiving the blade 28 in a generally snap-on fit arrangement, being provided with a blade-receiving fitting arrangement 80, generally complementary in form for receiving blade 28 which, as best viewed in FIGS. 2, 4 and 5, has a through aperture 82, for this purpose. Additionally, an overhang portion of the fitting 80, designated generally at reference numeral 84, overlies and engages a top surface of the blade 28 to hold the same firmly in engagement with the carrier 30.

In accordance with a feature of the invention, the spring-receiving compartment 60 includes a generally downwardly depending lip portion or retaining portion 86 which will be seen to have a downwardly flared, ramped or cam surface 88. Upon initial assembly or pre-assembly of the spring 34 with the spring-receiving compartment 60, the free end 52 of the spring is pre-stressed in the manner shown in FIGS. 6 and 7 and placed entirely within the compartment 60 and behind the retaining lip 86. This greatly facilitates assembly of the now preassembled carrier, blade and spring with the two halves or shells 24, 26 of the housing 22. Moreover, the clip 38 is also preassembled with the trigger post 37 of the carrier prior to assembly thereof with the housing halves or shells 24, 26.

Cooperatively, one of the housing halves or shells, and in the illustrated embodiment the shell or half 24, is provided with a loading means in the form of a projecting pin or post 90 which is configured and located for engaging and urging the spring free end 52 back outwardly of the lip 86 upon assembly of the housing with the carrier. The ramp-like or cam-like nature of the surface 88 of the lip 86 facilitates the disengagement of spring end 52 in this regard. Upon this initial movement of the spring end 52, the same is free to engage the abutment surface 42 as previously described with reference to FIGS. 2-4.

Upon assembly, it will be seen that the trigger post 36 extends through an aperture 92 provided therefor through the abutment surface or upper wall 42. In this regard, it will be seen that substantially one-half of the abutment surface 42 and throug aperture 92 is formed in each of the housing halves or shell members 24, 26. Accordingly, the clip member 38 also extends over and generally rests upon the upper surface of abutment surface or wall 42, with the actuating end 40 thereof, upon initial assembly, extending outwardly of a through aperture 94, provided therefor in the sidewall of the housing 22 (see FIG. 2).

Referring now to FIGS. 8–12, a retractable bleeding time lancet in accordance with a second embodiment of the invention is designated generally by the reference numeral 120. In many respects, the structure of the device of FIGS. 8–11 is similar to that previously described with reference to the embodiment shown in FIGS. 1–7. In this regard, the device 120 includes a housing 122 preferably formed of similar housing shells or halves 124, 126. Within the housing a blade 128 is mounted to a carrier means or member 130 which is in turn mounted for bi-directional sliding movement within the housing. The blade has a cutting edge 136, which in use is projected and retracted relative to a housing end opening 132.

A retention and release means or mechanism for the carrier 130 may be generally of the same form described hereinabove with reference to elements 37, 38 of FIGS. 1–7, and is not illustrated in FIGS. 8–12. That is, the carrier 130 may be provided with an upwardly projecting release pin or member 137 which cooperates with a suitable clip or other means (not shown) in an upper portion of the housing in much the same fashion as illustrated and described above with reference to FIGS. 1–7.

In similar fashion to the embodiment of FIGS. 1–7, the device 120 includes a resilient biasing means in the form of a similar coiled spring 34, which has a generally helical body portion 50, here mounted over a receiving pin or post 151, and generally oppositely outwardly projecting free ends or arms 152 and 154. The arm 152 is engaged or in abutment with an abutment surface comprising a pin 142, which functions similarly to the surface 42 in the embodiment of FIGS. 1–7.

The carrier 130 mounts the blade 128 by means of complementary receiving surfaces 180, 184 similar to those (80, 84) illustrated and described above with reference to the embodiment of FIGS. 1–7. Moreover, respective abutment surfaces or stop surfaces 146 of the housing 120, and 148 of the carrier 130, define the fully extended position of the carrier relative to the housing, for projecting the blade 128 outwardly thereof during use.

Departing from the embodiment of FIGS. 1–7, the driving force from the spring 134 is transmitted to the carrier 130 by means of a novel cam means or member 200. The cam member 200 will be seen to comprise a generally flat body portion 202 which is rotatably mounted to the housing 120 by a projecting shaft member or portion 204. In the illustrated embodiment, shaft 204 is formed on the cam 200; however, other arrangements for achieving this rotational mounting may be utilized without departing from the invention. The cam 200 further includes a first or driven projection or pin-like member or portion 206 which is engaged by the free end 154 of spring 134. A second, driving projection or pin-like member or portion 208 engages a first abutment surface 210 of the carrier. Projection 208 drives the carrier in a generally linear downward direction in response to the release of the spring and resulting force of the spring end 154 on projection 206, to achieve the first or initial portion of the compound movement of the carrier blade. This first or initial portion of compound movement is illustrated, for example, in FIG. 9, wherein the blade is shown in a fully extended position relative to the housing.

Figure 10:
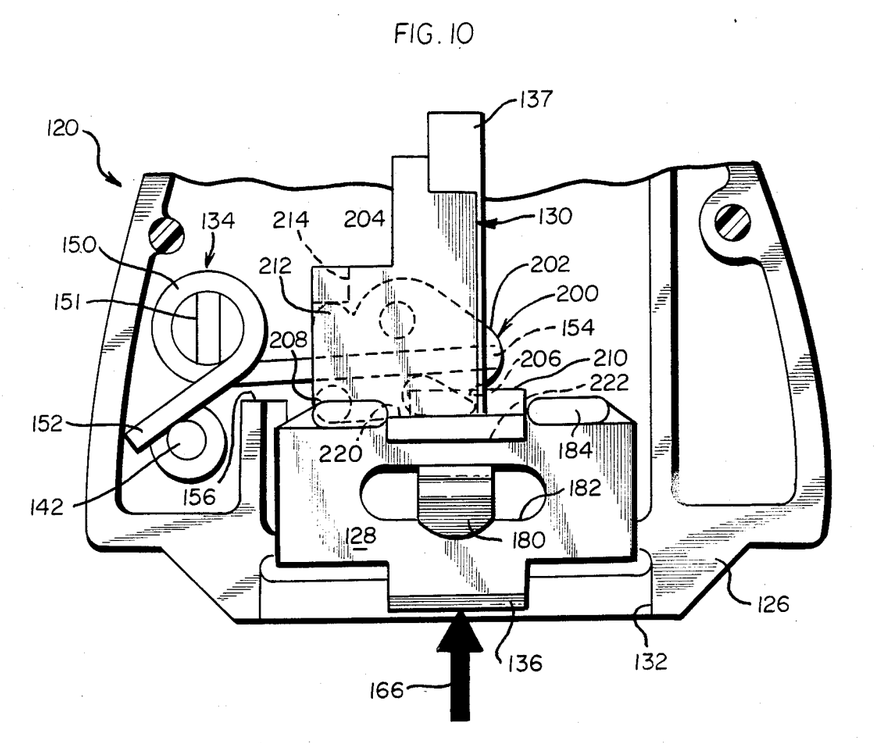
FIG. 10 is a view of the embodiment of FIGS. 8 and 9, and in similar fashion to FIG. 5, illustrating the second or retraction portion of the compound motion thereof.
Figure 11:
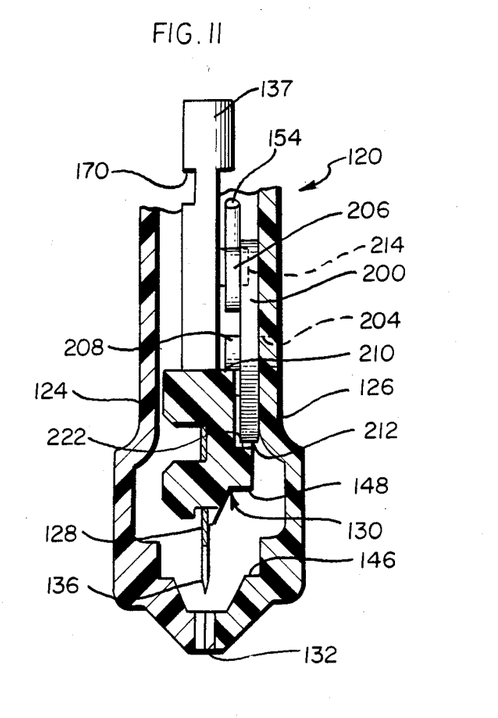
FIG. 11 is a partial sectional view taken generally in the plane of the line 11—11 of FIG. 8.
Figure 12:
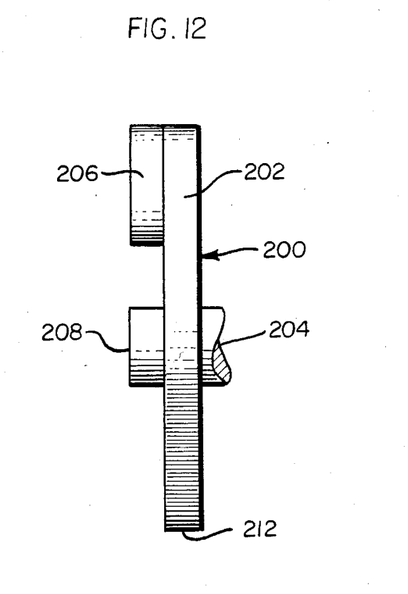
FIG. 12 is an enlarged end view of a cam member of the embodiment of FIGS. 8–11.

In order to achieve the second portion of compound motion, comprising retraction of the blade to a position substantially as shown in FIG. 10, the cam means or member 200 includes a return projection 212. Upon rotation of the cam 200 to the position shown in FIG. 9, it will be seen that return projection 212 approaches engagement with a second or return abutment surface or projection 214, formed on the carrier 130. Thereafter, as best viewed in FIG. 11, the continued rotation of the cam 200 causes engagement between surfaces or members 212 and 214, which results in slidable movement or lifting of the carrier 130 to retract the blade 128, and particularly the cutting edge 136 thereof, back within the housing 122. This retractive movement comprises the second portion of the compound motion previously described.

Figure 8:
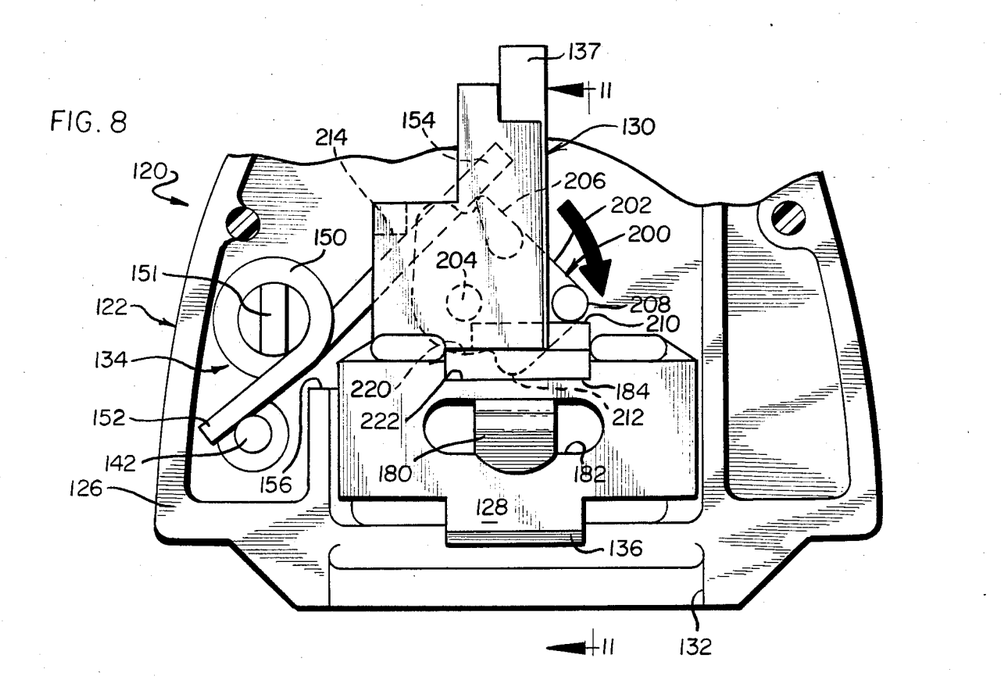
FIG. 8 is a view similar to FIG. 2, of a retractable lancet in accordance with a second embodiment of the invention, in its assembled condition and prior to use thereof.
Figure 9:
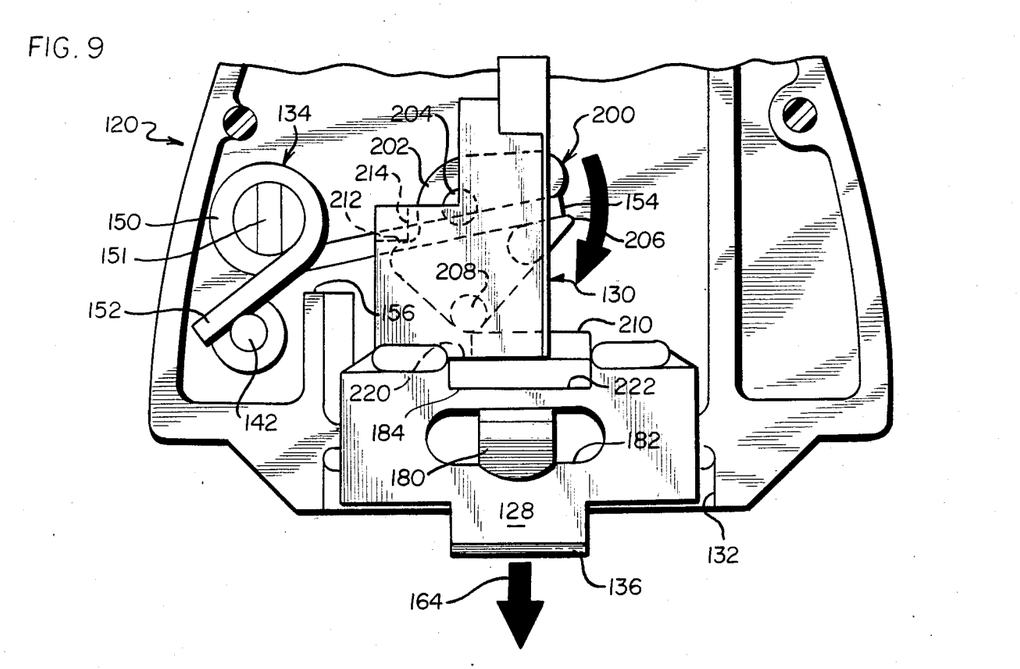
FIG. 9 is a view of the embodiment of FIG. 8, and in similar fashion to FIG. 4, illustrating a first portion of the compound motion of the blade thereof.

Moreover, it will be seen that like the embodiment of FIGS. 1–7, the device embodied in FIGS. 8–12 is non-resettable and non-reusable, since the internal components, spring, etc. are inaccessible for resetting back to the initial position shown in FIG. 8. Moreover, the blade is retracted within the housing following use, so that the device cannot be used manually, that is, without the spring-loaded controlled force and timing thereof. In the embodiment illustrated in FIGS. 8–12, the driven pin or projection member or portion 206 is generally teardrop-shaped to achieve the desired motion of the cam in response to the unwinding or release of tension on spring 134. Additionally, as best viewed in FIG. 11, it will be seen that a drop-off 220 is provided at the extreme end of abutment surface 210 to assure disengagement thereof by the pin or driving member 208 when it reaches the position illustrated in FIG. 10, so as to assure lifting of the carrier by the abutting of surfaces or members 212 and 214. Moreover, in order to provide clearance for the projection or return member or surface 212 during rotation of the cam 200, an additional relief area or cutaway portion 222 is also provided in the carrier 130.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim of the appended claims is to cover all such changes and modifications as fall within the true spirit and scope of the invention.

The invention is claimed as follows:

1. A retractable, non-reusable bleeding time lancet apparatus, comprising: a housing having an end opening; blade means; carrier means for fixedly mounting said blade means and mounted in said housing for sliding motion toward and away from said end opening; resilient biasing means comprising one and only one torsion spring mounted in said housing in a prestressed condition and operatively coupled for selectively and in sequence, urging said carrier means in opposite directions for achieving said sliding motion in a compound motion comprising, in sequence, motion first toward and then away from said housing end opening as said resilient biasing means goes from said prestressed condition toward an unstressed condition; non-resettable release means for initially retaining said biasing means in said prestressed condition and selectively activatable once and only once for releasing said resilient biasing means to urge said carrier means in said compound for momentarily projecting and then rapidly retracting at least a cutting edge of said blade means through said end opening; cooperating means on said housing and said carrier means for defining respective limits of sliding motion of said carrier means corresponding to extended and retracted positions of said blade means cutting edge relative to said housing end opening; and means operatively engaging said resilient biasing means with said carrier means for achieving said compound motion of said carrier means; said release means being operatively disengaged from said biasing means upon release thereof and incapable of re-engagement therewith; said compound motion comprising an initial portion including extension of said carrier means for projecting said blade means cutting edge outwardly of said housing end opening, immediately followed by a second portion including retraction of said carrier means for retraction of said blade means cutting edge back into said housing and for thereafter positively holding said blade within said housing to prevent further projection of said cutting edge outwardly of said end opening; and wherein said torsion spring comprises a coiled spring having a helical body and at least one outwardly projecting free end portion, and wherein said free end portion urges said carrier means in said compound motion.

2. Apparatus according to claim 1 wherein said means operatively engaging said biasing means for urging said carrier means comprises first and second abutment surfaces on said housing, each located a fixed distance from said end opening for respectively abutting said one free end portion of said coiled spring during said two portions of said compound motion and means defining a compartment within said carrier means for receiving the body portion of said coiled spring for thereby achieving said compound motion as said spring resiliently returns to a relaxed state upon activation of said release means and serially abuts said first and second abutment surfaces.

3. Apparatus according to claim 1 wherein said coiled spring comprises a helical body portion and respective outwardly projecting free end portions and wherein said means operatively engaging said biasing means for urging said carrier means comprises a first abutment surface on said housing for abutting one of said free ends of said coiled spring, and cam means engaged with the other of said free ends of said coil spring and operatively coupled with said carrier means for driving the same in said compound motion in response to release of said spring from its prestressed state by said release means.

4. Apparatus according to claim 1 wherein said housing is configured for maintaining said resilient biasing means inaccessible to prevent subsequent movement thereof back to said prestressed condition following a single release thereof, so as to thereafter retain the blade means cutting edge retracted within the housing and to prevent any subsequent extension thereof outwardly of the housing.

5. Apparatus according to claim 1 wherein said resilient biasing means comprises a spring configured for providing a predetermined, controlled amount of force and acceleration to said blade means for maintaining a controlled amount of force and time of contact of said blade means cutting edge with the skin of the patient.

6. Apparatus according to claim 1 wherein said resilient biasing means is operatively coupled to said carrier means for initially extending the carrier means upon activation of the release means, and for continuous movement toward an unstressed rest position so as to substantially immediately retract said carrier means as the prestressing force upon the spring is dissipated during travel toward said rest position, and for thereafter retaining said carrier means in a retracted condition relative to said housing.

7. Apparatus according to claim 2 wherein said first and second abutment surfaces are spaced, parallel, and mutually facing surfaces, the first abutment surface being located a first distance from said end opening, and said second abutment surface being located a second, smaller distance from said end opening.

8. Apparatus according to claim 2 wherein said torsion spring carrier means compartment includes a retaining lip portion for retaining said spring free end therewithin in said prestressed condition for permitting initial pre-assembly of said spring with said compartment, prior to assembly thereof with said housing.

9. Apparatus according to claim 8 wherein said housing includes preloading means for urging said spring free end out of engagement with said retaining lip portion of said carrier means and into engagement with said first abutment surface, upon assembly of the preassembled carrier means and spring with said housing.

10. Apparatus according to claim 9 wherein said housing comprises first and second complementary shell members and wherein said loading means comprises a projecting post on one of said shell members positioned for engagement with said spring free end upon assembly of said shell members about said preassembled carrier means and spring.

11. Apparatus according to claim 1 wherein said retaining means comprises an elongate trigger post extending integrally from said carrier means and clip means coupled with said housing and releasably engaged with said trigger post for normally holding said carrier means in a retracted position and for retaining said resilient means in said prestressed condition, and means for manually releasing said clip means from said engagement with said trigger post.

12. Apparatus according to claim 3 wherein said cam means comprises a substantially flat body portion rotatably mounted to said housing, a driven pin projecting from said body for engagement with said other end of said coil spring, a driving pin member projecting from said body for engagement with said carrier means for driving said carrier means in said first portion of said compound motion and a return portion projecting from said body for driving said carrier means in said second portion of said compound motion.

13. Apparatus according to claim 12 wherein said carrier means includes first and second abutment surfaces which are located in a substantially parallel and spaced apart condition, said first abutment surface being engaged by said driving pin member during said first portion of said compound motion and said second abutment surface being engaged by said return projection during said second portion of said compound motion.

14. A device according to claim 12 and further including means mounting said spring body to said housing.

15. A device according to claim 14 and further including an abutment surface formed on said housing for permanently abutting one of said free ends of said spring.

16. A mechanism for achieving compound motion of a member with respect to a housing, comprising: carrier means for fixedly mounting said member and mounted in said housing for bi-directional sliding motion; resilient biasing means comprising one and only one torsion spring mounted in said housing in a prestressed condition and operatively coupled for selectively urging said carrier means for achieving said bi-directional sliding motion as the said resilient biasing means goes from said prestressed condition toward an unstressed condition; non-resettable release means for normally retaining said biasing means in said prestressed condition and selectively activatable for releasing said resilient biasing means to urge said carrier means in said sliding motion; cooperating means on said housing and said carrier means for defining respective limits of sliding motion of said carrier means corresponding to opposite extreme positions of said carrier means relative to said housing; and means operatively engaging said resilient biasing means with said carrier means for achieving said compound motion of said carrier means; said release means being operatively disengaged from said biasing means upon release thereof and incapable of re-engagement therewith; said compound motion comprising an initial portion including urging of said carrier means to a first of said extreme positions, immediately followed by a second portion including urging of said carrier means toward said opposite extreme position, and for thereafter positively holding said member within said housing; and wherein said torsion spring comprises a coiled spring having a helical body portion and at least one outwardly projecting free end portion, and wherein said free end portion urges said carrier means in said compound motion.

17. Apparatus according to claim 16 wherein said means operatively engaging said biasing means for urging said carrier means comprises first and second spaced apart abutment surfaces on said housing, for respectively abutting said one free end portion of said coiled spring during said two portions of said compound motion and means defining a compartment within said carrier means for receiving the body portion of said coiled spring for thereby achieving said compound motion as said spring resiliently returns to a relaxed state upon activation of said release means and serially abuts said first and second abutment surfaces.

18. Apparatus acording to claim 16 wherein said torsion spring coiled spring comprising a helical body portion and respective outwardly projecting free end portions and wherein said means operatively engaging said biasing means for urging said carrier means comprises a first abutment surface on said housing for abutting one of said free ends of said coiled spring, and cam means engaged with the other of said free ends of said coiled spring and operatively coupled with said carrier means for driving the same in said compound motion in response to release of said spring from its prestressed state by said release means.

19. Apparatus according to claim 1 wherein said helical body defines an axis and wherein said operatively engaging means includes means for positioning said coiled spring such that its axis is substantially perpendicular to the direction of movement of said carrier means.

20. Apparatus according to claim 16 wherein said helical body defines an axis and wherein said operatively engaging means includes means for positioning said coiled spring such that its axis is substantially perpendicular to the direction of movement of said carrier means.

* * * * *